United States Patent [19]
Benkowski et al.

[11] Patent Number: 6,058,958
[45] Date of Patent: May 9, 2000

[54] PULSATILE FLOW SYSTEM AND METHOD

[75] Inventors: Robert J. Benkowski; Bryan E. Lynch, both of Houston, Tex.

[73] Assignee: MicroMed Technology, Inc., The Woodlands, Tex.

[21] Appl. No.: 09/187,560

[22] Filed: Nov. 5, 1998

[51] Int. Cl.[7] ................................................ G05D 7/00
[52] U.S. Cl. ............................ 137/14; 73/168; 137/563; 137/565.34; 137/593; 417/138; 417/141
[58] Field of Search .................................. 73/168; 137/14, 137/563, 565.34, 593; 417/137, 138, 141

[56] References Cited

U.S. PATENT DOCUMENTS

| | | | |
|---|---|---|---|
| 3,864,060 | 2/1975 | Hall et al. ............................. | 417/138 X |
| 4,321,017 | 3/1982 | Gottliebson ........................... | 417/138 X |
| 5,272,909 | 12/1993 | Nguyen et al. ......................... | 73/37 |
| 5,531,094 | 7/1996 | More et al. ............................. | 73/4 |

*Primary Examiner*—Gerald A. Michalsky
*Attorney, Agent, or Firm*—Howrey Simon Arnold & White, LLP

[57] ABSTRACT

The present invention relates to a pulsatile flow system and method. The pulsatile flow system includes a reservoir, a pressure riser and a first fluid passage connected between the reservoir and the pressure riser. The system further includes a device adapted to expel fluid from the reservoir through the first fluid passage to the pressure riser. A second fluid passage is connected between the pressure riser and the reservoir, and is adapted to allow fluid to flow unidirectionally therethrough, from the pressure riser to the reservoir. The pulsatile flow system may be adapted to provide pulsatile fluid flow through a medical device, such as a ventricle assist device or mechanical heart valve, to replicate a heart's pumping action for testing the device.

33 Claims, 3 Drawing Sheets

PULSATILE FLOW SYSTEM AND METHOD

BACKGROUND OF THE INVENTION

1. Field of the Invention

The invention relates generally to pulsatile flow systems, and more particularly, to s a pulsatile flow system that mimics the pumping of a human heart.

2. Description of Related Art

Systems that provide a pulsatile, or non-continuous, flow are used in a variety of applications. Such pulsatile flow systems are often employed for functional and reliability testing of medical devices designed to work in conjunction with a beating heart, for example, mechanical heart valves or implantable blood pumps.

Implantable blood pumps generally fall into two categories: total "artificial hearts," employed to completely replace a human heart which is not functioning properly; or "ventricle assist devices (VADs)," used to boost blood circulation in patients whose heart still functions but is not pumping blood at an adequate rate. Total artificial hearts completely replace a native heart. In contrast, VADs and mechanical valves designed to replace defective heart valves operate in conjunction with a native heart. Prior to implanting VADs or other mechanical devices in a patient to operate in conjunction with the patient's heart, it is desirable to insure that the devices operate properly and possess the required reliability characteristics. Such devices may be tested by operating them in a system that provides a pulsatile fluid flow therethrough, replicating the heart's pumping of blood.

The human heart beats more than 30 million times in a single year and pumps more than 4,300 gallons of blood a day. Thus, in an average lifetime of 70 years, the heart beats more than 2.5 billion times and pumps 1 million barrels of blood. Therefore, to obtain adequate reliability data on a VAD or other device that is to be operated with a beating heart, the device typically must be operated continuously for an extended time period.

Unfortunately, many existing pulsatile flow systems are not designed for such continuous, extended operation. Moreover, existing systems are often complicated and expensive. The estimated need for a long-term VAD is presently projected at between 50,000 and 100,000 patients per year in the United States alone. Thus, a need exists for a simple, yet reliable, pulsatile flow system for testing such devices.

The present invention addresses these, and other, shortcomings associated with the prior art.

SUMMARY OF THE INVENTION

In one aspect of the present invention, a pulsatile flow system includes a reservoir, a pressure riser and a first fluid passage connected between the reservoir and the pressure riser. The system further includes a device adapted to expel fluid from the reservoir through the first fluid passage to the pressure riser. A second fluid passage is connected between the pressure riser and the reservoir, and is adapted to allow fluid to flow unidirectionally therethrough, from the pressure riser to the reservoir.

In another aspect of the present invention, a method of providing a pulsatile fluid flow includes applying a force to fluid contained in a reservoir to expel fluid from the reservoir through a first flow passage to a pressure riser containing fluid, such that the level of the fluid contained in the pressure riser increases. The method further includes preventing fluid flow through a second flow passage between the pressure riser and the reservoir. The force is removed from the fluid contained in the reservoir, and fluid flow through the second flow passage from the pressure riser to the reservoir is permitted.

In a particular aspect of the invention, a method of life testing a ventricle assist device including an inlet and an outlet is presented. The method includes connecting the inlet to a reservoir containing fluid and connecting the outlet to a pressure riser containing fluid. A force is applied to the fluid in the reservoir to expel fluid from the reservoir, through the ventricle assist device, to the pressure riser. Fluid flow is prevented from the pressure riser to the reservoir through a return passage. The force is removed from the fluid in the reservoir, and fluid flow through the second flow passage is permitted from the pressure riser to the reservoir.

BRIEF DESCRIPTION OF THE DRAWINGS

Other objects and advantages of the invention will become apparent upon reading the following detailed description and upon reference to the drawings in which.

Figure 1:
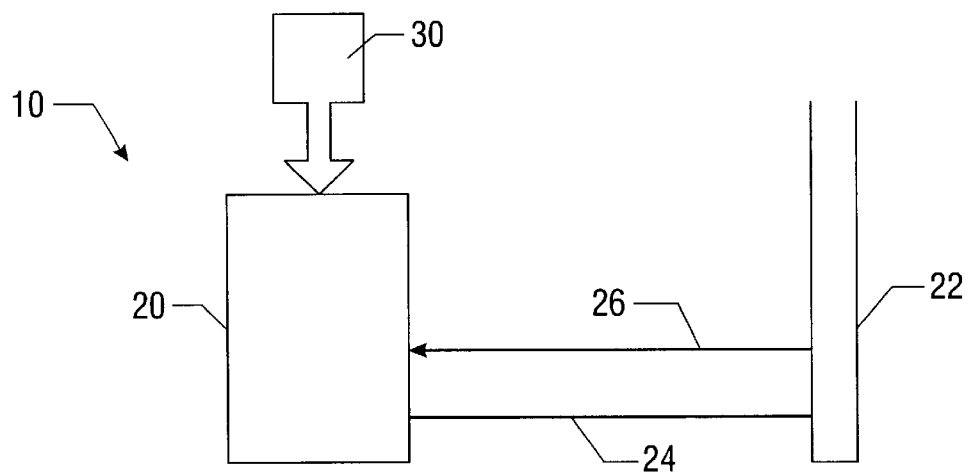
FIG. 1 is a block diagram, schematically illustrating a pulsatile flow system in accordance with the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning to the drawings and in particular, FIG. 1, a pulsatile flow system 10 in accordance with an embodiment of the present invention is schematically illustrated. The pulsatile flow system 10 includes a reservoir 20 and a pressure riser 22. Both the reservoir 20 and the pressure riser 22 are adapted to contain a volume of fluid. First and second flow passages 24, 26 are connected between the reservoir 20 and the pressure riser 22, such that the reservoir 20, the first flow passage 24, the pressure riser 22, and the second flow passage 26 form a loop through which fluid may circulate. The second flow passage 26 is adapted to allow fluid to flow unidirectionally therethrough, from the pressure riser 22 to the reservoir 20. A device 30 is adapted to expel fluid contained in the reservoir 20 through the first fluid flow passage to the pressure riser 22.

Figure 2:
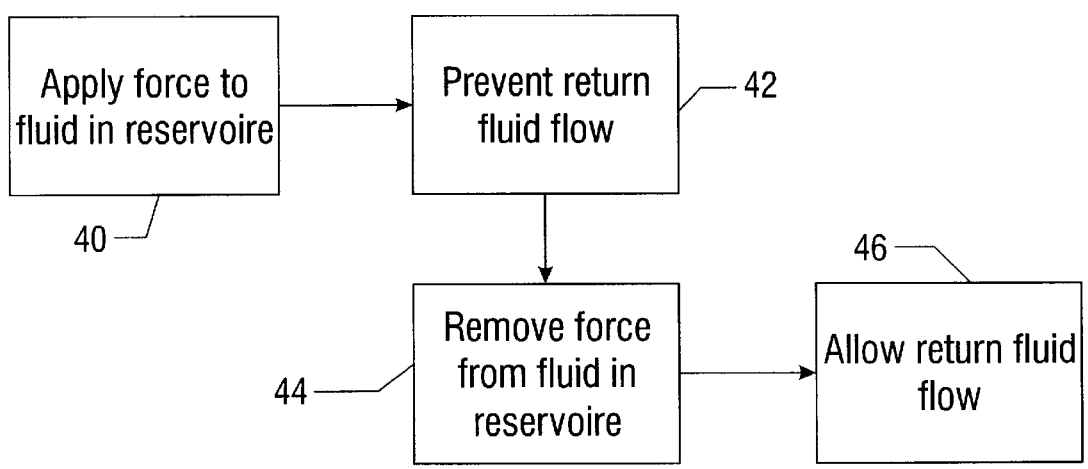
FIG. 2 is a flow diagram, illustrating a method of providing a pulsatile flow in accordance with an embodiment of the present invention.

FIG. 2 is a flow diagram, generally illustrating the operation of the pulsatile flow system 10 illustrated in FIG. 1. In block 40, the device 30 applies a force to fluid contained in the reservoir 20, so as to expel fluid from the reservoir 20. As disclosed above in conjunction with FIG. 1, the second fluid passage 26 is adapted to allow fluid to flow unidirectionally therethrough, from the pressure riser 22 to the reservoir 20. Thus, the fluid expelled from the reservoir 20 as a result of the force applied thereto (block 40) flows from the reservoir 20, through the first fluid passage 24 and into the pressure riser 22. As illustrated in block 42, return fluid flow through the second fluid passage 26 is prevented. Hence, the fluid flowing from the reservoir 20, through the first fluid passage 24 and into the pressure riser 22 raises the level of fluid contained in the pressure riser 22. In block 44, the device 30 removes the force from fluid contained in the reservoir 20, and in block 46, return fluid flow from the pressure riser 22 to the reservoir 20 is allowed through the second, or return fluid passage 26, thus returning the fluid level of the pressure riser 22 to its original level.

Figure 3:
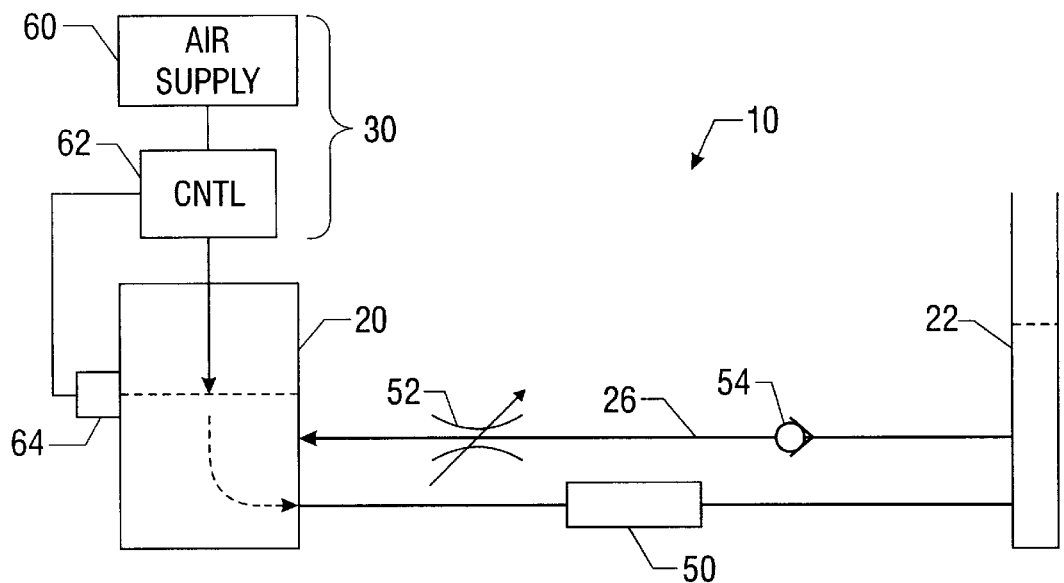
FIG. 3 is a block diagram, schematically illustrating the pulsatile flow system of FIG. 1, including additional components in accordance with other aspects of the present invention.

FIG. 3 schematically illustrates the pulsatile flow system 10, including additional components in accordance with other embodiments of the present invention. In the pulsatile flow system 10 illustrated in FIG. 3, the first fluid passage 24 is adapted to couple an apparatus 50 through which a pulsatile fluid flow is desired. For example, the pulsatile flow system 10, in accordance with aspects of the present invention, may be employed for functional or reliability testing of medical devices that operate in conjunction with a beating heart. The pulsatile flow system 10 may be configured, for example, to provide a pulsatile fluid flow, replicating the pulsatile flow of blood provided by a beating heart, through a mechanical heart valve or a ventricle assist device (VAD).

In the exemplary embodiment illustrated in FIG. 3, the second, or return fluid passage 26 includes a variable flow restrictor 52 that allows the return flow rate to be adjusted as desired. In other embodiments, the variable flow restrictor is mounted on the first fluid passage 24, or in still further embodiments, both the first and second fluid passages 24, 26 have a flow restrictor 52 mounted thereon, so that the flow rate through the pulsatile flow system 10 may be adjusted to a predetermined rate.

The return fluid passage 26 additionally includes a check valve 54 that is configured to allow unidirectional fluid flow through the return passage 26, from the pressure riser 22 to the reservoir 20. As illustrated in FIG. 3, the check valve 54 is configured such that, when a force is applied to fluid contained within the reservoir 20 (block 40 of FIG. 2), fluid flows from the reservoir 20, through the apparatus 50 and into the pressure riser 22. Moreover, the pressure of the fluid from the reservoir 20 causes the check valve 54 to close, preventing return fluid flow from the pressure riser 22 to the reservoir 20 (block 42 of FIG. 2). When the force applied to the fluid in the reservoir 20 is removed (block 44 of FIG. 2), the pressure on the pressure riser-side of the check valve 54 is greater than on the reservoir-side. Hence, the check valve 54 opens, allowing return fluid flow through the return fluid passage 26, from the pressure riser 22 to the reservoir 20.

In the embodiment illustrated in FIG. 3, the device 30 includes an air supply 60 configured to provide pressurized air to fluid contained in the reservoir 20, and further, a control device 62 operable to control the application of the pressurized air from the air supply 60 to fluid contained in the reservoir 20, so as to expel fluid from the reservoir 20 into the first fluid passage 24. The pulsatile flow system illustrated in FIG. 3 also includes a measurement device 64 adapted to measure the level of fluid contained in the reservoir, with the device 30 being responsive to the measurement device 64. Specifically, as illustrated in FIG. 3, the control device 62 is coupled to the measurement device 64, such that the control device 62 receives information regarding the level of fluid contained in the reservoir 20, and in response thereto, applies pressurized air from the air supply 60 to fluid contained in the reservoir 20 when the fluid reaches a predetermined level within the reservoir 20. In alternative embodiments, measurement devices may be applied to the pressure riser 22 in addition to, or in place of, the measurement device 64 coupled to the reservoir 20.

In accordance with various embodiments of the present invention, the measurement device 64 may comprise a number of different types of mechanisms. For example, the measurement device 64 may comprise one or more triggers coupled to the reservoir 20 or the pressure riser 22, or the triggers may be coupled to both the reservoir 20 and pressure riser 22. In one particular embodiment, a trigger is coupled to the reservoir 20 at a predetermined point on the side of the reservoir 20, and the trigger is activated when fluid within the reservoir reaches the predetermined point.

In accordance with one embodiment of the invention, the control device 62 includes a timer. When the trigger is activated in response to fluid within the reservoir 20 reaching the predetermined level, the control device 62 applies pressurized air to the fluid in the reservoir 20 for a predetermined time period, as indicated by the timer. When the predetermined time period has passed, the application of pressurized air is removed, and return flow from the pressure riser 22 to the reservoir 20 is permitted through the return fluid passage 26.

In accordance with another embodiment, at least two triggers are employed by the pulsatile flow system 10. The triggers may be coupled to either, or both, of the reservoir 20 and pressure riser 22. For instance, in such an embodiment using first and second triggers, the control device 62 may apply pressurized air from the air supply 60 to fluid contained in the reservoir 20 in response to activation of the first trigger, until the second trigger is activated.

Figure 4A:
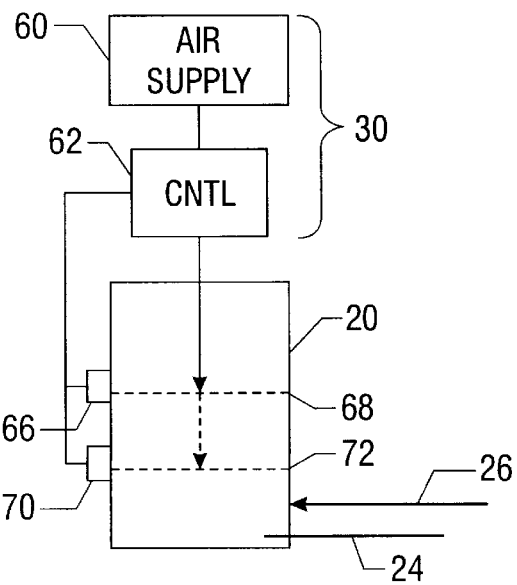
FIGS. 4A and B are block diagrams illustrating portions of pulsatile flow systems in accordance with alternative embodiments of the present invention.

More specifically, referring to FIG. 4A, a first trigger 66 is coupled to the reservoir 20 at a first predetermined point 68, such that the first trigger 66 is activated when the fluid level reaches the first predetermined point 68. Additionally, a second trigger 70 is coupled to the reservoir 20 at a second predetermined point 72, such that the second trigger 70 is activated when the fluid level reaches the second predetermined point 72. Thus, when the fluid level reaches the first predetermined point 68, the first trigger 66 is activated, and in response thereto, the control device 62 applies pressurized air from the air supply 60 to the fluid contained in the reservoir 20 to expel fluid from the reservoir 20 through the first fluid passage 24. The fluid is expelled from the reservoir 20 until it reaches the second predetermined point 72 and the second trigger 70 is activated. In response to the activation of the second trigger 70, the control device 62 stops applying the pressurized air to the fluid in the reservoir 20. Return flow is then allowed through the return passage 26, causing the fluid level to return to the first predetermined point 68, and the sequence repeats.

The triggers 66, 70 may comprise, for example, optical triggers, or mechanical triggers configured to operate in conjunction with float devices. As will be appreciated by one skilled in the art having the benefit of this disclosure, other types of trigger devices may be employed. Moreover, other types of measurement devices may be used for the measurement device 64. For example, a liquid level transmitter may be installed in one or both of the reservoir 20 and pressure riser 22 to provide a signal to the control device 62 indicating the fluid level. The control device 62 may then apply the pressurized air to fluid in the reservoir 20 when the level transmitter indicates that the fluid is at a first level, and cease application of the pressurized air when the level transmitter indicates that the fluid is at a second level.

Figure 4B:
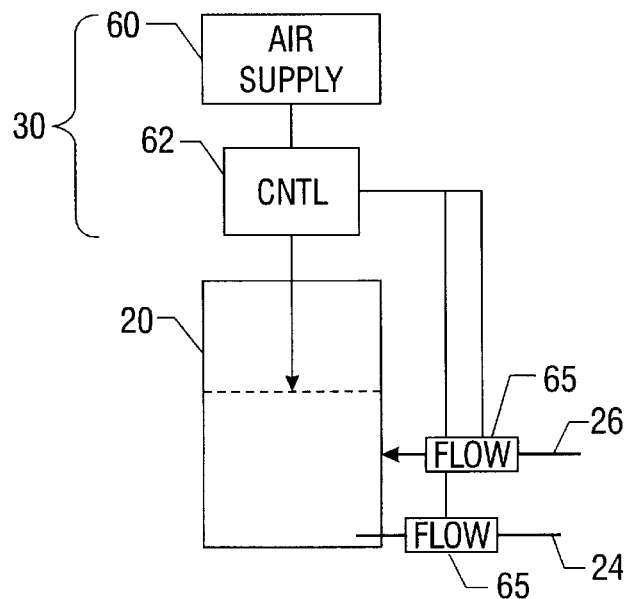

In a still further embodiment illustrated in FIG. 4B, the measurement device 64 may comprise one or more flow transducers 65 configured to measure fluid flow into the reservoir 20 through the first fluid passage 24, or fluid flow into the reservoir 20 through the second passage 26. In such an embodiment, the control device 62 applies pressurized air to the fluid in the reservoir 20 until a predetermined amount of fluid is expelled from the reservoir 20, as indicated by the flow transducer 65. When the predetermined amount of fluid has been expelled, the control device 62 ceases to apply the pressurized air, and the flow transducer 65 is reset. Return flow into the reservoir 20 is then allowed for a predetermined time period, or until a predetermined amount of fluid has returned to the reservoir 20.

Figure 5:
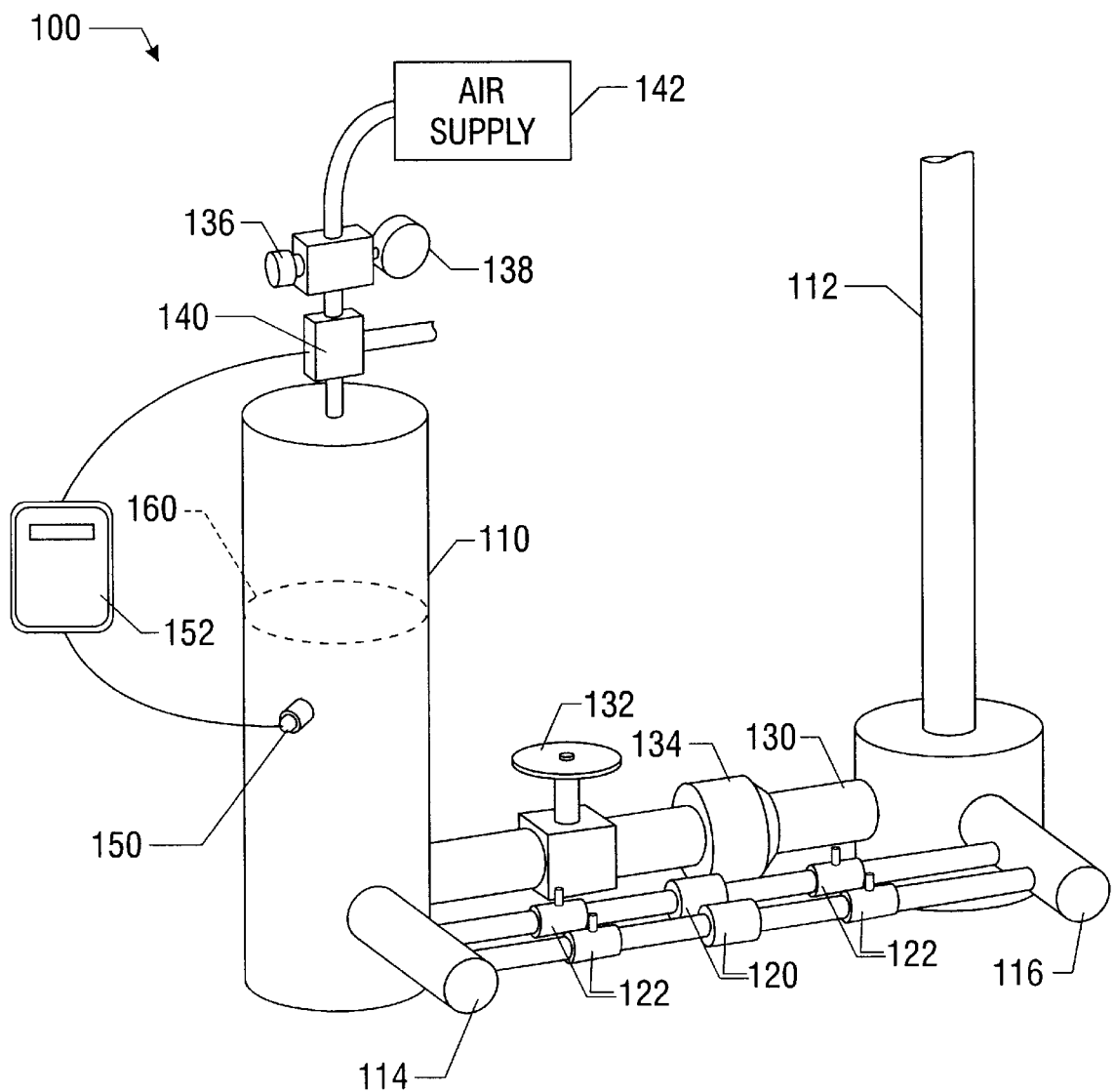
FIG. 5 illustrates a particular pulsatile flow system configured for life testing a ventricle assist device (VAD), in accordance with an embodiment of the present invention.

As discussed hereinabove, the pulsatile flow system 10 of the present invention is particularly well suited for functional or reliability testing of medical devices that operate in conjunction with a beating heart. FIG. 5 illustrates a specific embodiment of a pulsatile flow system 100 in accordance with the present invention, configured for life testing of one or more ventricle assist devices (VAD). Particularly, the pulsatile flow system 100 illustrated is adapted for life testing two VADs of the type disclosed in U.S. patent application Ser. No. 08/766,886, filed on Dec. 13, 1996, now U.S. Pat. No. 5,947,892, which is incorporated by reference herein in its entirety.

Referring to FIG. 5, the pulsatile flow system 100 includes a reservoir 110 and a pressure riser 112, both of which may be fabricated out of clear polyvinyl chloride (PVC) material. The reservoir 110 is analogous to the left ventricle of a human heart, with a static pressure of 10 mm Hg and a dynamic pressure representing left ventricle pressure during systole, or when the heart is contracting to pump blood. The pressure riser 112 provides resistance to fluid flow that is analogous to vascular resistance. In one configuration, the pressure riser 112 is 84 inches (213 cm) tall.

The inlet and outlet manifolds 114, 116 are coupled to the reservoir 110 and the pressure riser 112, respectively. The inlet and outlet manifolds 114, 116 may both be fabricated out of clear PVC. The inlet manifold 114 is adapted to couple the reservoir to the inlet of two VADs 120, and similarly, the outlet manifold 116 is adapted to couple the pressure riser to the outlet of the VADs 120. The system 100, as illustrated, is adapted for testing two VADs, though reconfiguring the pulsatile flow system 100 to test more or fewer VADs, or other devices, would be a routine undertaking for one skilled in the art having the benefit of this disclosure. Further, pressure taps 122, which may comprise Motorola MPX5050 pressure sensors, are coupled to the inlets and outlets of the VADs 120.

A return flow passage 130 is coupled between the pressure riser 112 and the reservoir 110 to provide unidirectional fluid flow therebetween. A variable rate flow restrictor 132 is situated in the return flow passage 130, which, for instance, may be used to adjust the flow rate in response to coupling additional VADs 120 to the inlet and outlet reservoirs 114, 116. The flow restrictor 132 functions to control simulated diastole duration. A Spears one-inch gate, PVC flow restrictor is one suitable flow restrictor. Further, a check valve 134 is situated in the return flow passage 130 to allow return flow from the pressure riser 112 to the reservoir 110, and prevent flow in the opposite direction, replicating the heart's mitral valve. In one application, the check valve 134 comprises a 27 mm mechanical valve available from CarboMedics, Inc.

A pressure regulator 136 and a pressure gauge 138 are connected between a three-way pneumatic solenoid 140 and an air supply 142. The pneumatic solenoid, which may comprise a Humphrey 320 solenoid, controls the application of pressurized air from the air supply 142 to fluid contained in the reservoir 110, and vents air from the reservoir 110 when fluid enters the reservoir 110 through the return fluid passage 130. A suitable pressure regulator 136 and pressure gauge 138 include an ARO Corp. 127122-300 pressure regulator and an ARO Corp. 29755-1 pressure gauge. An optical fluid level trigger 150, such as a GEM ELS-1100 trigger, is coupled to the reservoir 110, and a digital timer 152, available from Scientific Controls Research, is connected between the fluid level trigger 150 and the solenoid 140.

In a typical application of a VAD, the VAD pumps blood in conjunction with the patient's heart, to assist an ailing heart. The inlet of the VAD is connected to the patient's left ventricle to receive oxygenated blood therefrom, and the outlet of the VAD is connected to the patient's aorta, or another blood vessel, so that the VAD pumps oxygenated blood to be carried throughout the body. Referring to the embodiment of the invention illustrated in FIG. 5, to simulate the VAD's operation in conjunction with a beating heart, two VADs 120 are connected to the inlet and outlet manifolds 114, 116. The VADs 120 are operated so as to pump fluid from the reservoir 110 to the pressure riser 112, simulating the pumping of blood from the left ventricle to the body to assist a beating heart.

The pressure head in the pressure riser 112 causes the check valve 134 to open, simulating the operation of the mitral valve and allowing fluid to flow through the return passage 130 into the reservoir 110. At this point, the three-way pneumatic solenoid 136 is off, and air is vented from the reservoir 110 as fluid enters from the pressure riser 112.

When the fluid level in the reservoir 110 reaches the optical fluid level trigger 150, the timer 152 is activated, energizing the solenoid 136 which exposes the fluid in the reservoir 110 to regulated inlet air from the air supply 142 at a pressure between 5–10 PSI. In a particular embodiment, the reservoir includes a vapor barrier 160, situated within the reservoir 110 between the fluid and the air inlet into the reservoir, to reduce evaporation of fluid from the pulsatile flow system 100. In a system having a vapor barrier, which may comprise a diaphragm, the solenoid 136 provides pressurized air from the air supply 142 to the vapor barrier. The vapor barrier deflects toward the fluid, expelling fluid from the reservoir 110.

The application of the pressurized air so as to expel fluid from the reservoir 110 is analogous to the heart's ventricular contraction, or systole, which increases ventricular pressure and shuts the mitral valve. Referring to FIG. 5, when the air pressure starts expelling the fluid from the reservoir 110, the check valve 134 closes, preventing return s fluid flow through the return fluid passage 130 from the pressure riser 112 to the reservoir 110. The pressure at the inlets of the VAD 120 increases, and in turn, the flow through the VAD increases, as it would when a VAD is working in conjunction with a heart. The force of systole is controlled by the air inlet pressure, which is indicated by the pressure gauge 138 and regulated via the pressure regulator 136.

The fluid column height in the pressure riser 112 increases to about 120 mm Hg, increasing back pressure to the VAD similar to the elasticity and resulting back pressure caused by the arterial circulatory system. The timer 152 energizes the solenoid 136 for a predetermined time period, typically 0.3 to 0.6 seconds. The time period is determined based on the desired "heart rate," and on the desired ratio of systole time to diastole time.

To simulate diastole, or the ventricular relaxation phase, the solenoid 136 ceases to apply pressurized air to the fluid within the reservoir 110. Thus, the pressure difference across the VAD is high, due to the suddenly reduced inlet pressure and the increased outlet pressure resulting from the increased fluid level within the pressure riser 112. This high outlet pressure causes the check valve 134 to open, allowing return flow through the return passage 130, and the sequence repeats. The duration of diastole in the pulsatile flow system 100 is controlled by the flow regulator 132, which regulates the return flow rate from the pressure riser 112 to the reservoir 110. In the particular embodiment illustrated, the flow regulator 132 effectively controls the "heart rate" of the system 100, since the end of diastole is triggered by the fluid level in the reservoir 110.

In the embodiment of the pulsatile flow system 100 illustrated in FIG. 5, employing two VADs 120, the diameters of the reservoir 110 and the pressure riser 112 are sized so as to obtain the desired VAD outlet pressure levels using gravity and the fluid column contained in the pressure riser 112. Specifically, the reservoir 110 and the pressure riser 112 are sized such that the fluid column fluctuates between about 80 mm and 120 mm Hg, while the two VADs are each providing a mean flow of 5 liters per minute.

Thus, the present invention provides a simple and inexpensive, yet reliable and effective, system for providing a pulsatile fluid flow. The particular embodiments disclosed above are illustrative only, as the invention may be modified and practiced in different but equivalent manners apparent to those skilled in the art having the benefit of the teachings herein. For example, the system illustrated in FIG. 5 may be reconfigured for functional or life testing of a mechanical heart valve, or other such medical device. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A pulsatile flow system, comprising:
   a reservoir;
   a pressure riser;
   a first fluid passage connected between the reservoir and the pressure riser;
   a device adapted to expel fluid from the reservoir through the first fluid passage to the pressure riser; and
   a second fluid passage connected between the pressure riser and the reservoir, the second fluid passage adapted to allow fluid to flow unidirectionally therethrough, from the pressure riser to the reservoir.

2. The pulsatile flow system of claim 1, wherein at least one of the first and second fluid passages is adapted to restrict fluid flow to a predetermined rate.

3. The pulsatile flow system of claim 2, wherein at least one of the first and second fluid passages includes a flow restrictor valve.

4. The pulsatile flow system of claim 1, wherein the second flow passage includes a check valve configured to allow unidirectional fluid flow through the second passage, from the pressure riser to the reservoir.

5. The pulsatile flow system of claim 1, further comprising at least one device adapted to measure the level of fluid contained in the reservoir, wherein the device adapted to expel fluid is responsive to the at least one device adapted to measure the fluid level.

6. The pulsatile flow system of claim 1, wherein the device adapted to expel fluid comprises:
   an air supply configured to provide pressurized air to fluid contained in the reservoir; and
   a control device operable to control the application of the pressurized air to fluid contained in the reservoir so as to expel fluid from the reservoir into the first fluid passage.

7. The pulsatile flow system of claim 6, further comprising at least one level measurement device adapted to determine the level of fluid contained in the reservoir, wherein the control device is responsive to the level measurement device to apply the pressurized air to fluid contained in the reservoir when the fluid reaches a predetermined level.

8. The pulsatile flow system of claim 7, wherein:
   the at least one level measurement device comprises at least one trigger coupled to at least one of the reservoir and the pressure riser at a predetermined point, such that the trigger is activated when the fluid level reaches the predetermined point; and wherein
   the control device includes a timer and is operable to, upon activation of the trigger, apply the pressurized air to fluid contained in the reservoir for a predetermined time period as indicated by the timer.

9. The pulsatile flow system of claim 8, wherein the trigger comprises an optical trigger.

10. The pulsatile flow system of claim 7, wherein:
    the at least one level measurement device comprises
    a first trigger coupled to one of the inlet manifold or the pressure riser at a first predetermined point, such that the first trigger is activated when the fluid level reaches the first predetermined point; and
    a second trigger coupled to one of the inlet manifold or the pressure riser at a second predetermined point, such that the second trigger is activated when the fluid level reaches the second predetermined point; and wherein
    the control device is operable to, upon activation of the first trigger, apply pressurized air to fluid contained in the reservoir until the second trigger is activated.

11. The pulsatile flow system of claim 7, wherein:
    the at least one level measurement device comprises a fluid level transducer coupled to one of the reservoir or the pressure riser, the fluid level transducer adapted to output a signal to the control device indicating the level of fluid contained within at least one of the reservoir and the pressure riser; and wherein the control device is operable to apply pressurized air to fluid contained in the reservoir when the fluid level reaches a first predetermined level until the fluid level reaches a second predetermined level.

12. The pulsatile flow system of claim 6, further comprising a flow transducer adapted to output a signal to the control device indicating the amount of fluid expelled from the reservoir; wherein the control device is operable to apply pressurized air to fluid contained in the reservoir until a predetermined amount of fluid is expelled from the reservoir.

13. The pulsatile flow system of claim 6, wherein the control device is further adapted to vent air from the reservoir when fluid enters the reservoir through the fluid return passage.

14. The pulsatile flow system of claim 6, wherein the control device comprises a solenoid.

15. The pulsatile flow system of claim 6, further comprising a vapor barrier situated in the reservoir, the vapor barrier adapted to prevent direct contact between fluid contained in the reservoir and the pressurized air, the vapor barrier configured such that the pressurized air moves the vapor barrier to expel fluid from the reservoir.

16. The pulsatile flow system of claim 15, wherein the vapor barrier comprises a diaphragm.

17. The pulsatile flow system of claim 1, wherein the first fluid passage comprises a plurality of flow passages.

18. The pulsatile flow system of claim 17, further comprising:

a first manifold connected to the reservoir; and a second manifold connected to the pressure riser;

the first and second manifolds each adapted to couple the plurality of first flow passages between the reservoir and the pressure riser.

19. The pulsatile flow system of claim 1, wherein the first fluid passage is adapted to couple an apparatus through which a pulsatile fluid flow is desired between the reservoir and the pressure riser, so as to establish a flow path through the apparatus from the reservoir to the pressure riser.

20. The pulsatile flow system of claim 19, wherein the apparatus comprises a ventricle assist device.

21. The pulsatile flow system of claim 19, wherein the apparatus comprises a valve.

22. The pulsatile flow system of claim 19, wherein the first fluid passage comprises:

an inlet passage having a first end connected to the reservoir, and a second end adapted to be coupled to an inlet of the ventricle assist device; and an outlet passage having a first end coupled to the pressure riser, and a second end adapted to be coupled to an outlet of the ventricle assist device.

23. The pulsatile flow system of claim 22, further comprising at least one pressure sensor situated on at least one of the inlet or outlet passage.

24. The pulsatile flow system of claim 23, wherein the at least one pressure sensor comprises first and second pressure sensors; the first and second sensors being situated on the inlet and outlet passages, respectively.

25. A pulsatile flow system, comprising:

a reservoir;

a pressure riser;

first means for connecting at least one ventricle assist device between the reservoir and the pressure riser so as to establish a flow path therethrough;

second means for expelling fluid from the reservoir through the first fluid passage to the pressure riser; and a second fluid passage connected between the pressure riser and the reservoir, the second fluid passage including third means for allowing unidirectional flow therethrough, from the pressure riser to the reservoir.

26. The pulsatile flow system of claim 25, wherein the second means includes means for controlling the expulsion of fluid from the reservoir.

27. The pulsatile flow system of claim 25, wherein the second fluid passage includes means for regulating fluid flow rate therethrough.

28. A method of providing a pulsatile fluid flow, comprising:

applying a force to fluid contained in a reservoir to expel fluid from the reservoir through a first flow passage to a pressure riser containing fluid, such that the level of the fluid contained in the pressure riser increases;

preventing fluid flow through a second flow passage between the pressure riser the reservoir;

removing the force from the fluid contained in the reservoir; and permitting fluid flow through the second flow passage from the pressure riser to the reservoir.

29. The method of claim 28, wherein applying a force comprises applying pressurized air.

30. The method of claim 28, wherein preventing return flow comprises closing a check valve.

31. The method of claim 30, wherein applying a force to fluid contained in a reservoir to expel fluid from the reservoir further causes the check valve to close.

32. A method of life testing a ventricle assist device including an inlet and an outlet, comprising:

connecting the inlet to a reservoir containing fluid;

connecting the outlet to a pressure riser containing fluid;

applying a force to the fluid in the reservoir to expel fluid from the reservoir, through the ventricle assist device, to the pressure riser;

preventing fluid flow from the pressure riser to the reservoir through a return passage;

removing the force from the fluid in the reservoir; and permitting fluid flow through the return passage from the pressure riser to the reservoir.

33. The method of claim 32, wherein applying a force to the fluid in the reservoir comprises applying a force to the fluid in the reservoir to expel fluid from the reservoir, through the ventricle assist device, to the pressure riser so as to increase the outlet pressure from about 80 mm Hg to about 120 mm Hg.

\* \* \* \* \*